United States Patent [19]

Morikawa et al.

[11] Patent Number: 5,672,785
[45] Date of Patent: Sep. 30, 1997

[54] PROCESS FOR PRODUCING 1,1-DICHLORO-1,2,2,2-TETRAFLUOROETHANE

[75] Inventors: Shinsuke Morikawa, Yokohama; Shunichi Samejima, Tokyo; Masaru Yoshitake, Yokohama; Shin Tatematsu, Tokyo, all of Japan

[73] Assignee: Asahi Glass Company Ltd., Tokyo, Japan

[21] Appl. No.: 390,422

[22] Filed: Feb. 17, 1995

Related U.S. Application Data

[63] Continuation of Ser. No. 139,881, Oct. 22, 1993, abandoned, which is a continuation of Ser. No. 873,684, Apr. 24, 1992, abandoned, which is a continuation of Ser. No. 496,179, Mar. 20, 1990, abandoned, which is a continuation of Ser. No. 275,388, Nov. 23, 1988, abandoned.

[30] Foreign Application Priority Data

Nov. 26, 1987 [JP] Japan .................. 62-296182

[51] Int. Cl.$^6$ .................. C07C 17/37; C07C 17/358; C07C 17/20
[52] U.S. Cl. .................. 570/163; 570/151; 570/166; 570/167; 570/168
[58] Field of Search .................. 570/163, 151, 570/166, 167, 168

[56] References Cited

U.S. PATENT DOCUMENTS

| | | | |
|---|---|---|---|
| 1,970,562 | 8/1934 | Henne | 570/167 |
| 2,005,706 | 6/1935 | Daudt et al. | 570/167 |
| 2,005,707 | 6/1935 | Daudt et al. | 570/167 |
| 2,598,411 | 5/1952 | Miller et al. | 570/151 |
| 2,691,053 | 10/1954 | Woolf | 570/166 |
| 2,748,177 | 5/1956 | Miller et al. | 570/166 |
| 3,087,974 | 4/1963 | Hauptschein et al. | 570/151 |
| 3,398,202 | 8/1968 | Foulletier | 570/151 |
| 3,755,477 | 8/1973 | Firth et al. | 570/165 |
| 3,787,331 | 1/1974 | Groppelli et al. | 570/163 |
| 3,793,229 | 2/1974 | Groppelli et al. | 570/163 |
| 4,069,266 | 1/1978 | Komotsu et al. | 570/163 |
| 4,547,483 | 10/1985 | Muller et al. | 570/169 |
| 4,578,369 | 3/1986 | Muller et al. | 570/169 |
| 4,922,037 | 5/1990 | Manzer | 570/166 |
| 5,026,930 | 6/1991 | Manzer et al. | 570/168 |
| 5,051,537 | 9/1991 | Manzer | 570/168 |
| 5,146,020 | 9/1992 | Ruderhausen | 570/163 |

FOREIGN PATENT DOCUMENTS

| | | | |
|---|---|---|---|
| 1668346 | 4/1971 | Germany. | |
| 2245372 | 3/1974 | Germany. | |
| 4966 | 5/1969 | Japan | 570/168 |
| 921 796 | 3/1963 | United Kingdom. | |

OTHER PUBLICATIONS

Miller et al (II), "J. Am. Chem. Soc." vol. 72 (1950), pp. 705–707.
Vecchio et al.: J. of Fluorine Chem. 4(1974), pp. 117–139.
Kolditz et al.: Z. anorg. alig. Chem. 434 (1977), pp. 41–54.
Kolditz et al.: Z. anorg. align. Chem. 434 (1977), pp. 55–62.
Kolditz et al.: Z. anorg. align. Chem. 476 (1981), pp. 23–32.
Miller et al.: J. Am. Chem. Soc. 72 (1950), p. 705ff.
Kolditz et al.: Z. J. of Fluorine Chem. 5 (1975), pp. 141–151.
Beilsteins Handbuch der org. Chemie, E IV 1 (1972), pp. 136, 142.

Primary Examiner—G. Warren Ivy
Assistant Examiner—Lyman H. Smith
Attorney, Agent, or Firm—Oblon, Spivak, McClelland, Maier & Neustadt, P.C.

[57] ABSTRACT

A process for producing 1,1-dichloro-1,2,2,2-tetrafluoroethane, which comprises isomerizing 1,1,2-trichloro-1,2,2-trifluoroethane to form 1,1,1-trichloro-2,2,2-trifluoroethane, followed by fluorination with hydrofluoric acid.

14 Claims, No Drawings

PROCESS FOR PRODUCING 1,1-DICHLORO-1,2,2,2-TETRAFLUOROETHANE

This application is a Continuation of application Ser. No. 08/139,881, filed on Oct. 22, 1993, which is a Continuation of application Ser. No. 07/873,684, filed on Apr. 24, 1992, now abandoned, which is a Continuation of application Ser. No. 07/496,179, filed on Mar. 20, 1990, now abandoned, which is a Continuation of application Ser. No. 07/275,388, filed on Nov. 23, 1988, now abandoned.

The present invention relates to a process for producing 1,1-dichloro-1,2,2,2-tetrafluoroethane.

For the production of 1,1-dichloro-1,2,2,2-tetrafluoroethane (R-114a), a method is known wherein a haloethane such as 1,1,2-trichloro-1,2,2-trifluoroethane ($CCl_2FCClF_2$) is fluorinated. In this case, the reaction product will be a mixture of 1,1-dichloro-1,2,2,2-tetrafluoroethane (R-114a) and 1,2-dichloro-1,1,2,2-tetrafluoroethane (R-114).

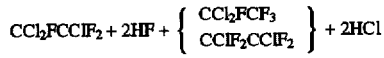

This may be attributable to the facts that during the fluorination, the substitution between the fluorine atom in hydrogen fluoride and the chlorine atom in 1,1,2-trichloro-1,2,2-trifluoroethane (R-113) does not necessarily preferentially take place at the $CClF_2$ side and that the isomerization rate from 1,2-dichloro-1,1,2,2-tetrafluoroethane (R-114) to 1,1-dichloro-1,2,2,2-tetrafluoroethane (R-114a) is small. Among the isomers of chlorofluorocarbons, the difference in the boiling points is rather small in many cases. This is true as between 1,1-dichloro-1,2,2,2-tetrafluoroethane (R-114a) and 1,2-dichloro-1,1,2,2-tetrafluoroethane (R-114), which have the boiling points of 3.0° C. and 3.8° C., respectively. Thus, the separation of the products is difficult. Accordingly, it is presently difficult to obtain a high purity product of 1,1-dichloro-1,2,2,2-tetrafluoroethane (R-114a) at low costs.

It is an object of the present invention to provide a novel process for producing highly pure 1,1-dichloro-1,2,2,2-tetrafluoroethane (R-114a).

The present invention provides a process for producing 1,1-dichloro-1,2,2,2-tetrafluoroethane (R-114a), which comprises isomerizing 1,1,2-trichloro-1,2,2-trifluoroethane (R-113) to form 1,1,1-trichloro-2,2,2-trifluoroethane (R-113a), followed by fluorination with hydrofluoric acid.

Among haloethanes of the formula $C_2Cl_{(6-n)}F_n$ wherein n is an integer of from 1 to 4, 1,1,2-trichloro-1,2,2- trifluoroethane (R-113) is most suitable as starting material especially from the economical view point since it is produced and sold in a large amount for a cleaning solvent used for the preparation of semi-conductor products. In order to obtain highly pure 1,1-dichloro-1,2,2,2-tetrafluoroethane (R-114a), it is necessary to adopt a reaction route and reaction conditions under which 1,2-dichloro-1,1,2,2-tetrafluoroethane (R-114), i.e. the isomer having an extremely close boiling point, is not substantially produced as a by-product. From the study of the behavior of R-113 in the isomerization and disproportionation, it has been found that the isomerization rate from R-113 to R-113a is higher than the disproportionation rate to R-112a and R-114a. Accordingly, it has been found possible to produce highly pure R-114a at low costs by optimizing the catalyst and reaction conditions in the reaction route which comprises the isomerization of R-113, followed by the fluorination.

The present inventors have conducted extensive researches on the reaction conditions including the isomerization catalysts and fluorination catalysts based on the results of the above study and have finally found a process for producing highly pure R-114a at high efficiency by using R-113 as starting material.

Now, the reaction of the present invention will be described in detail.

In the present invention, as the isomerization catalyst, a halide or oxide containing at least one element selected from the group consisting of Al, Cr, Mg, Ca, Sr, Ba, Fe, Ni and Co, may be employed. From the viewpoint of acid resistance and maintenance of the catalytic activities, it is preferred to employ oxides such as $Al_2O_3$, $Cr_2O_3$, MgO and CaO and mixed oxides thereof, or halides such as $AlCl_3$ and $CrCl_3$.

In the present invention, as the fluorination catalyst, a halide or oxide containing at least one element selected from the group consisting of Al, Cr, Mg, Ca, Sr, Ba, Fe, Ni, Co, Sb, Nb, Mn and Ta, may be employed. When a gas phase fluorination method is employed, it is preferred to employ oxides such as $Al_2O_3$, $Cr_2O_3$, MgO and CaO and mixed oxides thereof. When a liquid phase fluorination method is employed, it is preferred to employ halides such as $TaF_5$, $NbCl_5$ and $SbCl_5$.

All of the above catalysts are preferably activated with hydrogen fluoride or with a halogenated methane or halogenated ethane containing at least one fluorine atom such as R-11 or R-12, before they are used for the respective reactions.

The isomerization reaction is conducted usually within a temperature range of from 50 to 550° C., preferably from 100 to 400° C., under normal or elevated pressure in gas phase or under normal or elevated pressure in liquid phase.

The contact time is usually from 0.1 to 300 seconds, preferably from 5 to 30 seconds, in the case where the reaction is conducted in gas phase. In a case where the reaction is conducted in liquid phase, the retention time in the reactor is usually from 0.1 to 10,000 minutes, preferably from 10 to 1,000 minutes.

In order to maintain the catalytic activities, it is preferred that oxygen or chlorine is present in an amount of from 0.1 to 10% relative to R-113.

The fluorination reaction is conducted usually within a temperature range of from 50 to 550° C., preferably from 50 to 450° C., under normal or elevated pressure in gas phase, or under elevated pressure in liquid phase. The ratio of hydrogen fluoride to R-113a may be varied to a large extent. However, it is usual to use hydrogen fluoride in its stoichiometric amount for the substitution of the chlorine atom. Hydrogen fluoride may be used in an amount considerably larger than the stoichiometric amount relative to the total mols of the starting materials, for example, in an amount of 4 mols or larger. The contact time is usually from 0.1 to 300 seconds, preferably from 5 to 30 seconds, in the case where the reaction is conducted in gas phase. When the reaction is conducted in liquid phase, the retention time in the reactor is usually from 0.1 to 10,000 minutes, preferably from 10 to 1,000 minutes.

As mentioned above, in order to maintain the catalytic activities, it is preferred that oxygen or chlorine is present in an amount of from 0.1 to 10% relative to R-113a.

The reaction system may be of liquid phase or of gas phase. For a continuous reaction system, the apparatus can be simplified by conducting both the isomerization reaction and the fluorination reaction in gas phase. The desired product of the present invention can be separated by a usual method such as fractional distillation. By-products such as R-113a, 1,1,2,2-tetrachloro-1,2-fluoroethane (R-112) and 1,1,1,2-tetrachloro-2,2-fluoroethane (R-112a) may be recycled to the reaction system.

As described in the foregoing, the present invention provides a process for producing highly pure 1,1-dichloro-1,2,2,2-tetrafluoroethane (R-114a) by the isomerization of R-113, followed by fluorination.

Now, the present invention will be described in further detail with reference to Examples. However, it should be understood that the present invention is by no means restricted by such specific Examples.

PREPARATION EXAMPLE 1

1,100 g of guaranteed reagent $Al(NO_3)_3 \cdot 9H_2O$, 125 g of $Cr(NO_3)_3 \cdot 9H_2O$ and 10 g of $Mg(NO_3)_2 \cdot 6H_2O$ were dissolved in 2.5 L of water. This solution and 2,000 g of a 28% ammonium hydroxide aqueous solution were added to 4 L of hot water under stirring to obtain precipitates of hydroxides. The precipitates were collected by filtration, washed with deionized water and dried. Then, they were calcined at 450° C. for 5 hours to obtain a powder of oxides. The powder was formed into a cylindrical catalyst having a diameter of 5 mm and a height of 5 mm by means of a tabletting machine. The catalyst thus obtained was activated by fluorination at a temperature of from 200 to 400° C. in a gas mixture stream of hydrogen fluoride/nitrogen prior to the reaction.

PREPARATION EXAMPLES 2 TO 4

Catalysts were prepared in the same manner as in Preparation Example 1 except that 40 g of $Ba(NO_3)_2$, 50 g of $Sr(NO_3)_2$ and 40 g of $Ca(NO_3) \cdot 4H_2O$ were used, respectively, instead of $Mg(NO_3)_2 \cdot 6H_2O$.

PREPARATION EXAMPLE 5

A catalyst was prepared in the same manner as in Preparation Example 1 except that 300 g of $Fe(NO_3)_2 \cdot 9H_2O_2$ and 900 g of $Al(NO_3)_3 \cdot 9H_2O$ were used instead of $Al(NO_3)_3 \cdot 9H_2O$, $Cr(NO_3)_3 \cdot 9H_2O$ and $Mg(NO_3)_2 \cdot 6H_2O$.

PREPARATION EXAMPLE 6

A catalyst was prepared in the same manner as in Preparation Example 1 except that 600 g of $Fe(NO_3)_2 \cdot 9H_2O_2$ and 150 g of $Cr(NO_3)_3 \cdot 9H_2O$ were used instead of $Al(NO_3)_3 \cdot 9H_2O$, $Cr(NO_3)_3 \cdot 9H_2O$ and $Mg(NO_3)_2 \cdot 6H_2O$.

PREPARATION EXAMPLE 7

A catalyst was prepared in the same manner as in Preparation Example 1 except that 150 g of $Cr(NO_3)_3 \cdot 9H_2O$ and 1,300 g of $Al(NO_3)_3 \cdot 9H_{2O}$ were used instead of $Al(NO_3)_3 \cdot 9H_2O$, $Cr(NO_3)_3 \cdot 9H_2O$ and $Mg(NO_3)_2 \cdot 6H_2O$.

PREPARATION EXAMPLE 8

A catalyst was prepared in the same manner as in Preparation Example 1 except that 500 g of $Cr(NO_3)_3 \cdot 9H_2O$ and 160 g of $Mg(NO_3)_2 \cdot 6H_2O$ were used instead of $Al(NO_3)_3 \cdot 9H_2O$, $Cr(NO_3)_3 \cdot 9H_2O$ and $Mg(NO_3)_2 \cdot 6H_2O$.

PREPARATION EXAMPLE 9

200 g of $AlCl_3$ was dissolved in 2 liter of water. To this solution, 1,000 g of commercially available γ-alumina was added, and the mixture was dried to remove water. Further, the dried product was activated in the same activation method as in Preparation Example 1.

PREPARATION EXAMPLE 10

A catalyst was prepared in the same manner as in Preparation Example 9 except that 200 g of $CrCl_3 \cdot 6H_2O$ was used instead of $AlCl_3$. The catalyst was activated in the same activation method as in Preparation Example 1.

PREPARATION EXAMPLE 11

A catalyst was prepared in the same manner as in Preparation Example 9 except that 200 g of $MnCl_2 \cdot 4H_2O$ was used instead of $AlCl_3$. The catalyst was activated in the same activation method as in Preparation Example 1.

PREPARATION EXAMPLE 12

A catalyst was prepared in the same manner as in Preparation Example 9 except that 1,000 g of commercially available granular active carbon for catalyst carrier was used instead of γ-alumina. The catalyst was activated in the same activation method as in Preparation Example 1.

PREPARATION EXAMPLE 13

A catalyst was prepared in the same manner as in Example 10 except that 1,000 g of commercially available granular active carbon for catalyst carrier was used instead of γ-alumina. The catalyst was activated in the same activation method as in Preparation Example 1.

EXAMPLE 1

Inconel 600 U-shaped reactor tubes having an inner diameter of 2.54 cm and a length of 100 cm were used as reactors for isomerization and fluorination. A reactor packed with 200 cc of the γ-alumina catalyst activated in the same manner as in Preparation Example 1 was used as the reactor for the first isomerization reaction. A reactor packed with 200 ml of the fluorination catalyst prepared in the same manner as in Preparation Example 1 was used as the reactor for the second fluorination reaction. The first and second reactions were continuously conducted. To the first reactor, gasified 1,1,2-trichloro-1,2,2-trifluoroethane was supplied at a rate of 100 ml/min, and chlorine was supplied at a rate of 2 ml/min, and the reactor was held at 250° C. To the second reactor, hydrogen fluoride was supplied at a rate of 100 ml/min, and the reactor was held at 320° C. After removing acid components, the gas composition was analyzed by gas chromatography and $^{19}$F-NMR. The results are shown in Table 1.

TABLE 1

| Gas composition at the outlet of the reactor | Molar ratio (%) |
| --- | --- |
| R-114a | 72.0 |
| R-114 | 1.7 |
| R-113a | 17.3 |
| R-113 | 4.5 |
| Others | 4.5 |

EXAMPLE 2

The reaction was conducted under the same condition as in Example 1 except that the fluorination reaction temperature was changed to 350° C. After removing acid components, the gas composition was analyzed. The results are shown in Table 2.

TABLE 2

| Gas composition at the outlet of the reactor | Molar ratio (%) |
| --- | --- |
| R-114a | 72.2 |
| R-114 | 2.1 |
| R-113a | 13.1 |
| R-113 | 7.5 |
| Others | 7.1 |

EXAMPLES 3 TO 14

The catalysts prepared in Preparation Examples 1 to and r-alumina used in Example 1 were used as catalysts.

The reactions were conducted under the same conditions as in Example 1 except that the isomerization catalyst and the reaction temperature, and the fluorination catalyst and the reaction temperature were changed as shown in Table 3. The results are shown in Table 3.

TABLE 3

| Example Nos. | Isomerization catalyst | Reaction temp. (°C.) | Fluorination catalyst | Reaction temp. (°C.) | Gas composition at the outlet of the reactor (molar ratio %) | | | | |
| --- | --- | --- | --- | --- | --- | --- | --- | --- | --- |
| | | | | | 114a | 114 | 113a | 113 | Others |
| 3 | $Fe_2O_3Al_2O_3$ | 280 | $Cr_2O_3MgOAl_2O_3$ | 320 | 68.0 | 2.5 | 15.5 | 4.8 | 9.2 |
| 4 | $Cr_2O_3BaOAl_2O_3$ | 300 | $Cr_2O_3BaOAl_2O_3$ | 300 | 68.0 | 2.5 | 15.9 | 3.6 | 10.0 |
| 5 | $Cr_2O_3SrOAl_2O_3$ | 300 | $Cr_2O_3SrOAl_2O_3$ | 300 | 62.0 | 4.4 | 18.8 | 8.5 | 6.3 |
| 6 | $Cr_2O_3CaOAl_2O_3$ | 300 | $Cr_2O_3CaOAl_2O_3$ | 300 | 70.5 | 5.8 | 14.2 | 5.4 | 4.1 |
| 7 | $Fe_2O_3Cr_2O_3$ | 300 | $Fe_2O_3Cr_2O_3$ | 300 | 67.8 | 5.9 | 13.7 | 6.4 | 6.2 |
| 8 | $Al_2O_3$ | 250 | $Fe_2O_3Cr_2O_3$ | 350 | 72.5 | 1.6 | 19.8 | 3.2 | 2.9 |
| 9 | $Cr_2O_3Al_2O_3$ | 250 | $Cr_2O_3Al_2O_3$ | 320 | 69.3 | 2.8 | 14.6 | 6.8 | 6.5 |
| 10 | $Cr_2O_3MgO$ | 250 | $Cr_2O_3MgO$ | 300 | 63.8 | 5.2 | 12.7 | 3.4 | 14.9 |
| 11 | $Al_2O_3$ | 250 | $Al_2O_3$ | 350 | 46.3 | 8.4 | 22.9 | 3.5 | 18.9 |
| 12 | $Al_2O_3$ | 250 | $MnCl_2/Al_2O_3$ | 350 | 48.5 | 7.7 | 21.4 | 6.8 | 15.6 |
| 13 | $AlCl_3/Al_2O_3$ | 250 | $CrCl_3/Al_2O_3$ | 350 | 67.8 | 3.3 | 16.1 | 4.3 | 8.5 |
| 14 | $AlCl_3/C$ | 250 | $CrCl_3/C$ | 350 | 63.8 | 3.7 | 24.1 | 4.2 | 4.2 |

EXAMPLE 15

Into a Hastelloy C autoclave having an internal capacity of 1 liter, 20 g of aluminum chloride and 600 ml of 1,1,2-trichloro-1,2,2-trifluoroethane were introduced and maintained at 80° C. for 7 hours. After cooling, the mixture was transferred to another Hastelloy C autoclave having an internal capacity of 1 liter, and 20 g of antimony pentachloride was added thereto. The mixture was heated to 120° C. Then, hydrogen fluoride was supplied at a rate of 50 g/hr for 4 hour, and the mixture was maintained for further 4 hours. After removing acid components, the gas composition was analyzed in the same manner as in Example 1. The results are shown in Table 4.

TABLE 4

| Gas composition at the outlet of the reactor | Molar ratio (%) |
| --- | --- |
| R-114a | 60.0 |
| R-114 | 5.2 |
| R-113a | 27.3 |
| R-113 | 4.5 |
| Others | 3.0 |

EXAMPLE 16

An Inconel 600 U-shaped reactor tube having an inner diameter of 2.54 cm and a length of 100 cm was used as the reactor for isomerization. The reactor packed with 200 cc of the alumina catalyst activated in the same manner as in the Preparation Examples was used as the reactor for isomerization. A condenser was connected to the outlet of the reactor, and a pump was provided so that the reaction mixture was introduced into a reactor of the second fluorination reaction (a Hastelloy C autoclave having a capacity of 1 liter) containing 20 g of antimony pentachloride. The reactions were conducted continuously. To the first reactor, gasified 1,1,2-trichloro-1,2,2-trifluoroethane was supplied at a rate of 100 ml/min, and chlorine was supplied at a rate of 2 ml/min. The reaction system was maintained at 250° C. To the second reactor, hydrogen fluoride was supplied at a rate of 20 g/hr, and the system was maintained at a temperature of 120° C. After removing acid components, the gas composition was analyzed by gas chromatography and $^{19}F$-NMR. The results are shown in Table 5.

TABLE 5

| Gas composition at the outlet of the reactor | Molar ratio (%) |
| --- | --- |
| R-114a | 58.0 |
| R-114 | 1.1 |
| R-113a | 20.8 |
| R-113 | 19.4 |
| Others | 0.7 |

EXAMPLE 17

Into a Hastelloy C autoclave having an internal capacity of 1 liter, 20 g of aluminum chloride powder and 600 ml of 1,1,2-trichloro-1,2,2-trifluoroethane were introduced and maintained at 80° C. for 7 hours. After cooling, the crude reaction solution was subjected to filtration. The successive fluorination reaction was conducted by using an Inconel 600 U-shaped tube having an inner diameter of 2.54 cm and a length of 100 cm as the reactor. The reactor packed with 200 ml of the fluorination catalyst prepared in the same manner as in Preparation Example 1 was used for fluorination. The crude reaction solution of the first reaction was gasified and supplied to the second reactor at a rate of 100 ml/min, chlorine supplied at a rate of 2 ml/min, and hydrogen fluoride was supplied at a rate of 100 ml/min. The reaction system was held at 320° C. After removing acid components, the gas composition was analyzed by gas chromatography and $^{19}$F-NMR. The results are shown in Table 6.

TABLE 6

| Gas composition at the outlet of the reactor | Molar ratio (%) |
| --- | --- |
| R-114a | 68.8 |
| R-114 | 4.7 |
| R-113a | 12.3 |
| R-113 | 11.2 |
| Others | 3.0 |

COMPARATIVE EXAMPLE 1

An Inconel 600 U-shaped reactor tube having an inner diameter of 2.54 cm and length of 100 cm was used as the reactor for fluorination. The reactor packed with 200 ml of the catalyst prepared in the same manner as in Preparation Example 1, was used as the reactor for fluorination. To the reactor, gasified 1,1,2-trichloro-1,2,2-trifluoroethane was supplied at a rate of 100 ml/min, chlorine was supplied at a rate of 2 ml/min, and hydrogen fluoride was supplied at a rate of 100 ml/min. The reaction system was held at 320° C. After removing acid components, the gas composition was analyzed. The results are shown in Table 7.

TABLE 7

| Gas composition at the outlet of the reactor | Molar ratio (%) |
| --- | --- |
| R-114a | 15.3 |
| R-114 | 61.1 |
| R-113a | 1.5 |
| R-113 | 8.5 |
| Others | 13.6 |

As is evident from the foregoing Examples, the present invention provides an advantage that 1,1-dichloro-1,2,2,2-tetrafluoroethane (R-114a) which used to be hardly available as a high purity product, can readily be produced in good yield from R-113 used as starting material.

We claim:

1. A process for producing 1,1-dichloro-1,2,2,2-tetrafluoroethane, which comprises:

1) isomerizing and disproportionating 1,1,2-trichloro-1,2,2-trifluoroethane to form a mixture comprising 1,1,1-trichloro-2,2,2-trifluoroethane, 1,1,1,2-tetrachloro-2,2-difluoroethane and 1,1-dichloro-1,2,2,2-tetrafluoroethane;

2) introducing said mixture from step 1) into a reactor; and 3) fluorinating said mixture from step 1) comprising 1,1,1-trichloro-2,2,2-trifluoroethane, 1,1,1,2-tetrachloro-2,2-difluoroethane and 1,1-dichloro-1,2,2,2-tetrafluoroethane with hydrofluoric acid.

2. The process of claim 1, wherein said fluorination is conducted in the presence of an activated fluorination catalyst selected from the group consisting of an oxide and a halide, wherein said oxide contains at least one element selected from the group consisting of Al, Cr, Mg, Ca, Sr, Ba, Fe, Ni, Co, Sb, Nb, Mn and Ta, and said halide contains at least one element selected from the group consisting of Cr, Mg, Ca, Sr, Ba, Fe, Ni, Co, Sb, Nb, Mn and Ta;

wherein said oxide catalyst is activated with hydrogen fluoride or with a halogenated methane or halogenated ethane containing at least one fluorine atom, before it is used for said fluorination.

3. A process for producing 1,1-dichloro-1,2,2,2-tetrafluoroethane, which comprises:

1) isomerizing and disportionation 1,1,2-trichloro-1,2,2-trifluoroethane in the presence of an activated catalyst comprising a halide or an oxide of at least one element selected from the group consisting of Al, Cr, Mg, Ca, Sr, Ba, Fe, Ni and Co to form 1,1,1-trichloro-2,2,2-trifluoroethane, 1,1,1,2-tetrachloro-2,2-difluoroethane and 1,1-dichloro-1,2,2,2-tetrafluoroethane;

2) introducing said mixture from step 1) into a reactor; and 3) fluorinating said mixture from step 1) comprising 1,1,1-trichloro-2,2,2-trifluoroethane, 1,1,1,2-tetrachloro-2,2-difluoroethane and 1,1-dichloro-1,2,2,2-tetrafluoroethane in the presence of an activated catalyst selected from the group consisting of an oxide and a halide, with hydrofluoric acid thereby yielding the desired product, wherein said oxide contains at least one element selected from the group consisting of Al, Cr, Mg, Ca, Sr, Ba, Fe, Ni, Co, Sb, Nb, Mn and Ta, and said halide contains at least one element selected from the group consisting of Cr, Mg, Ca, Sr, Ba, Fe, Ni, Co, Sb, Nb, Mn and Ta;

wherein said oxide catalyst is activated with hydrogen fluoride or with a halogenated methane or halogenated ethane containing at least one fluorine atom, before it is used.

4. The process of claim 1, wherein said isomerization and disproportionation reaction is conducted at a temperature of from 50° to 550° C.

5. The process of claim 1, wherein said fluorination catalyst is activated $Cr_2O_3MgOAl_2O_3$.

6. The process according to claim 1, wherein the isomerization and disproportionation is conducted in the presence of an isomerization catalyst comprising a halide or oxide of at least one element selected from the group consisting of Al, Cr, Mg, Ca, Sr, Ba, Fe, Ni and Co.

7. The process according to claim 1, wherein the isomerization and disproportionation is conducted at a temperature of from 50° to 550° C. under normal or elevated pressure in gas phase or under normal or elevated pressure in the liquid phase.

8. The process according to claim 1, wherein the fluorination is conducted at a temperature of from 50° to 550° C. under normal or elevated pressure in the gas phase, or under elevated pressure in the liquid phase.

9. The process according to claim 7, wherein said isomerization and disproportionation reaction is conducted at a temperature of from 100° to 400° C.

10. The process according to claim 6, wherein contact between said isomerization and disproportionation catalyst and reactant 1,1,2-trichloro-1,2,2-trifluoroethane ranges from 0.1 to 300 seconds.

11. The process according to claim 5, wherein said fluorination reaction is conducted at a temperature ranging from 50 to 450° C.

12. The process according to claim 1, wherein contact between said catalyst and said 1,1,1-trichloro-2,2,2-trifluoroethane reactant ranges from 0.1 to 300 seconds.

13. The process according to claim 6, wherein during said isomerization and disproportionation, the isomerization and disproportionation reaction is conducted under conditions which maintain an amount of oxygen or chlorine ranging from 0.1 to 10% relative to 1,1,2-trichloro-1,2,2-trifluoroethane.

14. The process according to claim 1, wherein during said fluorination, the fluorination reaction is conducted such that the amount of oxygen or chlorine ranges from 0.1 to 10% relative to said 1,1,1-trichloro-2,2,2-trifluoroethane.

* * * * *